United States Patent [19]
Scheinberg

[11] Patent Number: 6,067,987
[45] Date of Patent: *May 30, 2000

[54] PROTECTING SKIN AND OTHER TISSUES FROM FRICTION

[75] Inventor: Samuel Scheinberg, Otis, Oreg.

[73] Assignee: The Seaberg Company, Inc., Newport, Oreg.

[ * ] Notice: This patent is subject to a terminal disclaimer.

[21] Appl. No.: 09/268,888

[22] Filed: Mar. 16, 1999

Related U.S. Application Data

[63] Continuation-in-part of application No. 09/039,742, Mar. 16, 1998, Pat. No. 5,899,207.

[51] Int. Cl.[7] .................................................. A61F 5/37
[52] U.S. Cl. ............................................ 128/882; 128/889
[58] Field of Search .................................. 128/845, 846, 128/888, 889, 893, 894

[56] References Cited

U.S. PATENT DOCUMENTS

| | | | |
|---|---|---|---|
| 1,913,928 | 6/1933 | Kaufman . | |
| 2,098,312 | 11/1937 | Scholl . | |
| 2,261,041 | 10/1941 | Tennant | 128/894 |
| 2,712,311 | 7/1955 | Scholl | 128/894 |
| 2,918,062 | 12/1959 | Scholl | 128/894 |
| 3,062,208 | 11/1962 | Scholl | 128/894 |
| 3,260,261 | 7/1966 | Gallovich . | |
| 3,548,420 | 12/1970 | Spence . | |
| 3,821,954 | 7/1974 | Grubel | 128/149 |
| 3,968,530 | 7/1976 | Dyson | 5/338 |
| 4,572,174 | 2/1986 | Eilender et al. | 128/149 |
| 4,959,059 | 9/1990 | Eilender et al. | 604/358 |
| 5,012,801 | 5/1991 | Feret | 128/155 |
| 5,188,124 | 2/1993 | Feret | 128/889 |
| 5,462,519 | 10/1995 | Carver | 602/47 |

*Primary Examiner*—Michael A. Brown
*Attorney, Agent, or Firm*—Cernoff, Vilhauer McClung & Stenzel, L.L.P.

[57] ABSTRACT

A tissue-protective device (16, 18, 20, 60, 66, 76, 86, 96, 110, 130) and a method for protecting tissue against abrasion by attaching a pair of mutually overlying membranous layers (26, 28, 122, 124) to an area of a tissue surface such as a person's skin with only the peripheries of the layers interconnected with each other, so that the layers can easily slip along each other. An absorbent pad (88, 98) may be placed between one of the layers and the tissue, and may be impregnated with medication to be delivered to the tissue being protected. A quantity of a lubricant can be contained between the layers. The device is thin, to avoid causing pressure when it is used in restricted spaces, as within one's shoe. The device can also be implanted internally as where tendons move along an implanted plate.

20 Claims, 3 Drawing Sheets

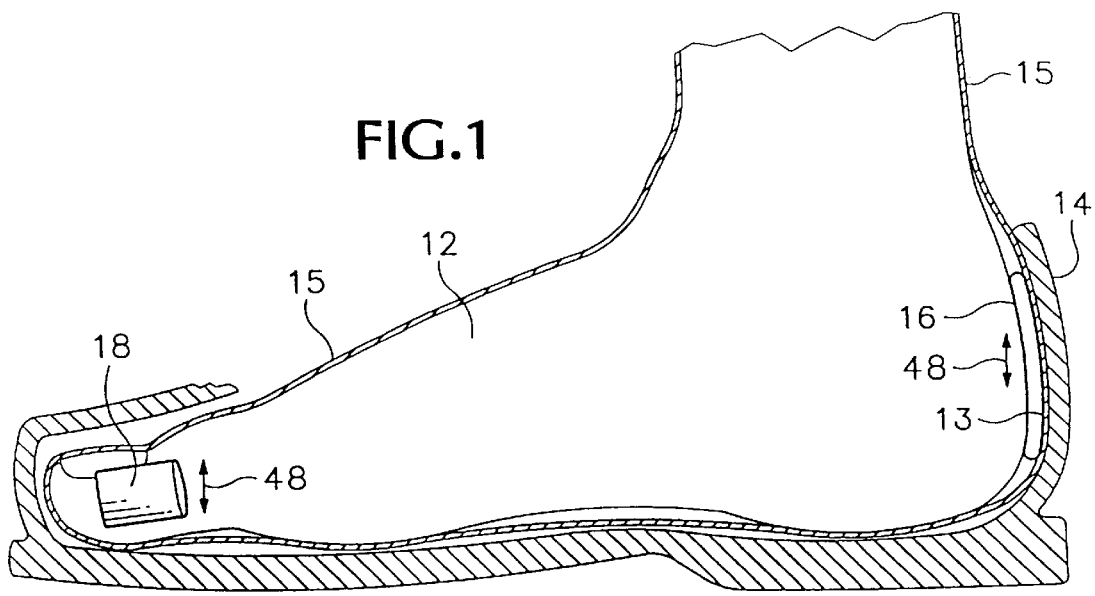
FIG.1
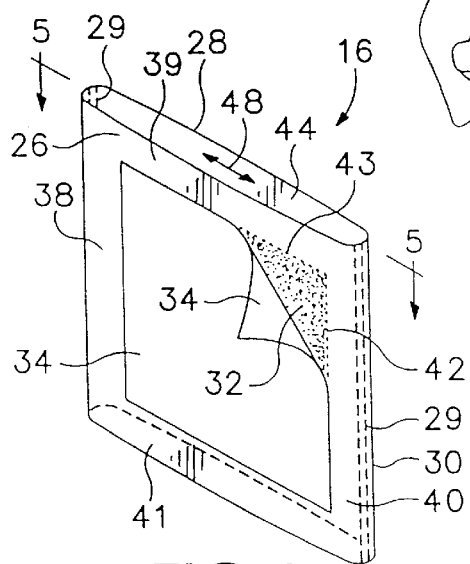
FIG.4
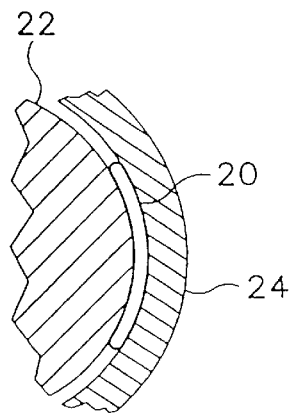
FIG.2
FIG.3
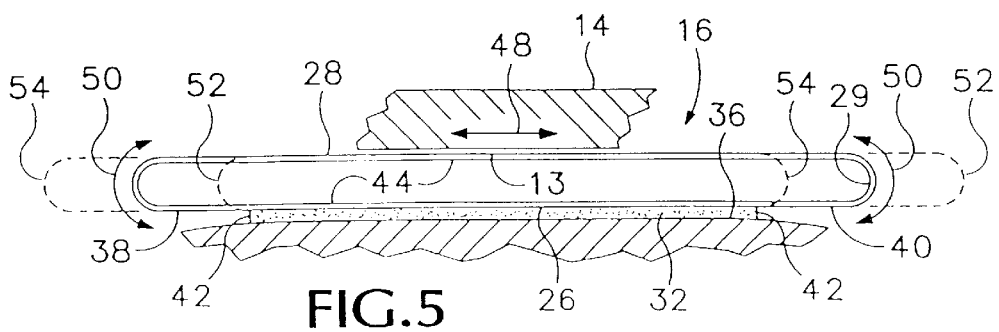
FIG.5

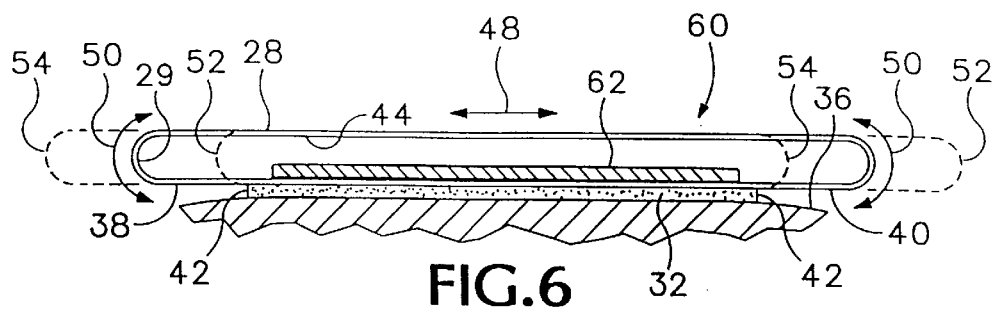
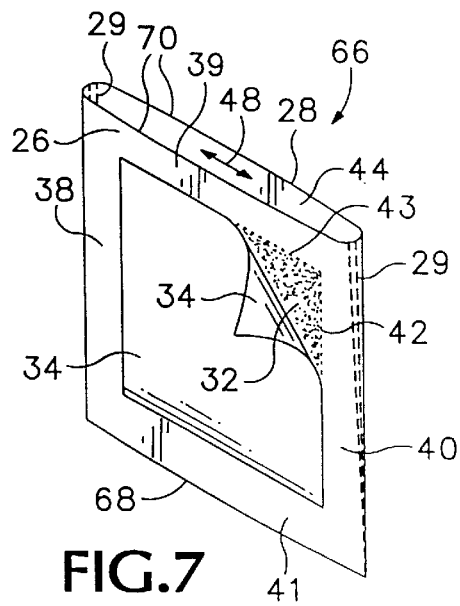
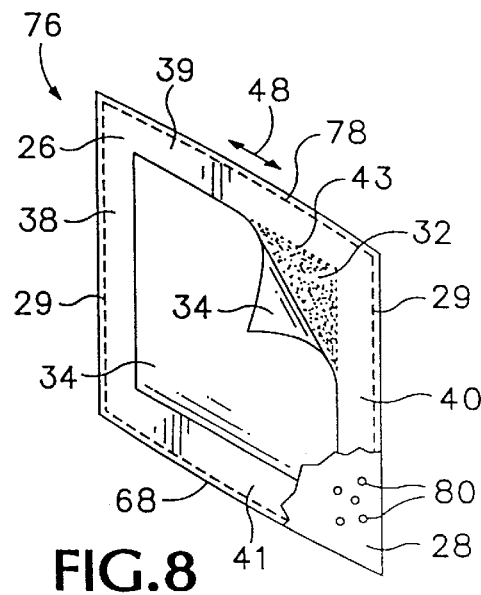
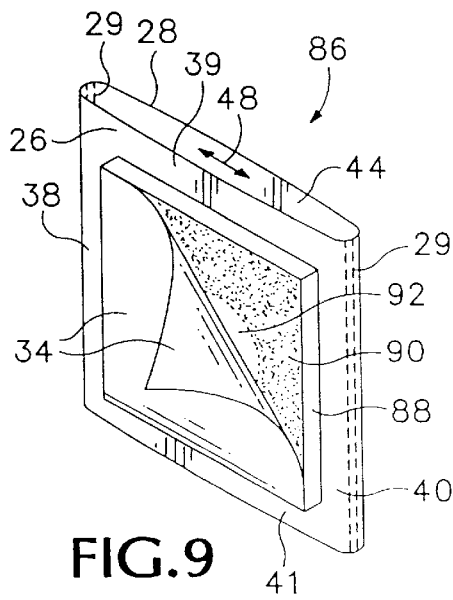
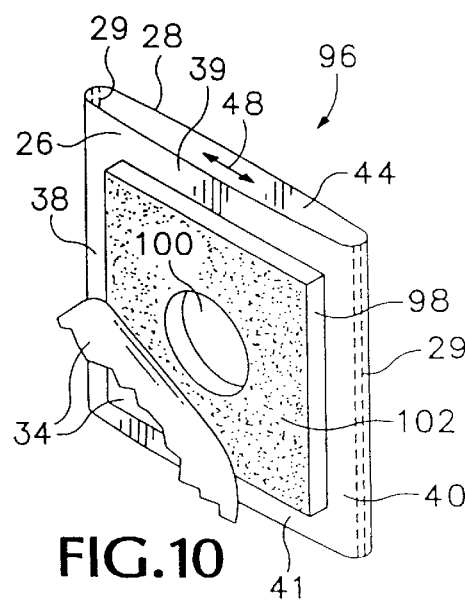

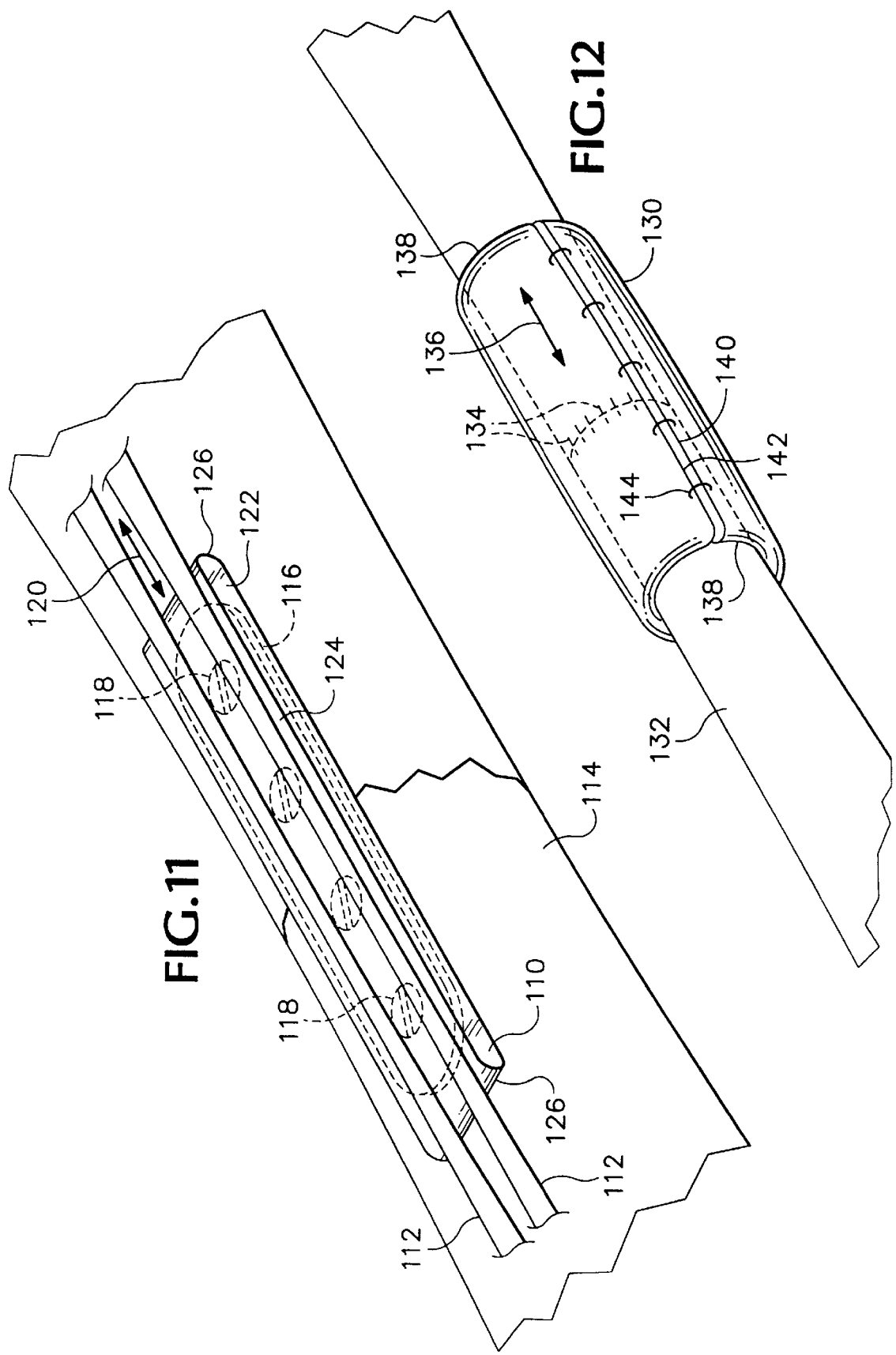

PROTECTING SKIN AND OTHER TISSUES FROM FRICTION

This application is a continuation-in-part of copending U.S. patent application Ser. No. 039,742, filed Mar. 16, 1998, now U.S. Pat. No. 5,899,207.

BACKGROUND OF THE INVENTION

The present invention relates to avoidance and treatment of irritation resulting from friction or pressure against an area of skin, and from friction where internal tissue repair has been accomplished by surgery.

It is well known that poorly fitting shoes, gloves, and other clothing can rub a person's skin and thereby cause significant irritation, soreness, or blisters, or may rub away a portion of the skin's surface. Such irritation by friction can be caused by straps of undergarments, by the rubbing of casts on the skin thinly covering a joint, such as a person's wrist within such a cast, or by athletic clothing or equipment rubbing a person's skin, as when a person is riding a bicycle or performing other physically demanding exercise over an extended time, particularly when there is pressure against the skin. Soreness may also be caused by friction against the skin of person in a wheelchair or confined to bed for a long time.

Attempts to avoid injury of skin by such friction in the past have included the use of devices intended to slip easily along the surface of the skin, as disclosed in Eilender et al. U.S. Pat. Nos. 4,959,059 and 4,572,174. Approaching the problem in another way, dressings intended to slip easily over adjacent materials are disclosed in Feret U.S. Pat. Nos. 5,012,801 and 5,188,124.

Various other devices have been intended to protect an irritated area of a person's skin by providing a structure supported by adjacent skin to push irritant surfaces away from irritated skin, or to equalize pressure on areas of a person's skin likely to be irritated. Such devices are disclosed in Kaufman U.S. Pat. No. 1,913,928, Scholl U.S. Pat. No. 2,098,312, Spence U.S. Pat. No. 3,548,420, Grubel U.S. Pat. No. 3,821,954, Gallovich U.S. Pat. No. 3,260,261, and Dyson U.S. Pat. No. 3,968,530. An inflatable pad for protecting bedsores is disclosed by Carver U.S. Pat. No. 5,462,519.

The devices disclosed in the patents mentioned above, however, have not proved entirely satisfactory, for various reasons. Many of the devices previously known have acted as pads, but have not satisfactorily protected skin against the effects of friction and pressure against an adjacent surface. Such friction causes the skin to be pulled in directions parallel to its surface, generating shear forces within the skin that eventually irritate and cause injury to the skin, despite the use of the previously known devices for protecting the skin. Additionally, the previously known devices, with few exceptions, have had a thickness which of itself increases the pressure of an adjacent surface against skin in many situations, such as where a shoe fits poorly.

In some instances where tissues have been repaired surgically within a patient's body, it is also desirable to avoid friction. For example, when a distal radial fracture is reduced by implanting a plate held in place by screws, overlying tendons at times rub uncomfortably on the implanted hardware. Where tendons have been grafted or repaired, the sutured tissue may attempt to adhere to surrounding tissues during the healing process, and such adherence is undesirable.

Consequently, what is still needed is an improved device for protecting a person's skin, or certain internal tissues in the vicinity of surgically repaired tissues, from the causes of friction. Preferably such an improved device should be thin, to avoid adding to pressure on the skin or other tissues needing protection, should greatly reduce friction between the skin or such other tissues and an adjacent surface, should be easily and cheaply manufactured, and should be easy to use.

SUMMARY OF THE INVENTION

The present invention overcomes the shortcomings of the prior art devices mentioned above and provides an improved device for protecting a person's skin and certain other tissues from injury or irritation, as well as a method of protecting one's skin or such other tissues by use of such a device. The protective device of the present invention is thin and in one preferred embodiment includes a pair of overlying layers of thin flexible membranous material attached to one another only at peripheral locations, leaving the two layers free to slip relative to each other with very little opposing friction, in response to relative movement between a person's skin and an adjacent surface of clothing, a cast or the like. The device is attached to the skin or the adjacent surface by an adhesive.

In one preferred embodiment of the invention the overlying flexible layers are provided in the form of an open-ended length of a flattened thin-walled tube of synthetic plastic material. In that embodiment of the invention the overlying layers of membranous material are interconnected along a pair of parallel opposite margins of each. A layer of an adhesive material attached to an outer surface of one of the layers has an area smaller than the area of each layer, so that marginal portions of the layers extend beyond the margins of the layer of adhesive material in at least two opposite directions.

In another embodiment of the invention the overlying layers are interconnected along the entire periphery of each layer, and a small amount of a lubricating material is located between the layers.

In one embodiment of the invention the overlying layers are of a thin breathably porous membranous material.

In another embodiment of the device according to the present invention a thin pad impregnated with useful substances such as antibiotics may be included between overlying membrane layers of suitably porous material to allow such useful substances to leach out into the surrounding tissue to protect an operative wound from infection.

In a further embodiment of the invention, a thin pad of absorbent material is located between the layer of adhesive material and the outer surface of one of the overlying membrane layers and may be used to carry medication to the surface of the skin, or to absorb fluids from the skin.

In yet a further embodiment of the invention a thin pad of cushioning material may define an opening to receive a raised portion of the skin, such as a blister.

According to the method of the invention, skin is protected against irritation by attaching a device such as one of those previously described to a person's skin, or to an adjacent surface, or between two adjacent layers of clothing or equipment that move relative to each other and one of which bears on the skin, and thereby significantly reducing friction resulting from such movement, so that the relative movement does not cause an irritating amount of stress on the skin adjacent the device.

According to a further aspect of the invention, a device constructed in accordance with the invention can be used similarly in accordance with the method of the invention in connection with surgical repair of tissue in situations where movement of internal tissue is likely, relative to an adjacent surface. For example, a device according to the invention could be used in accordance with the method of the invention to protect a muscle or tendon where a plate has been installed to stabilize a healing bone fracture, or to ensure continued mobility of a repaired tendon.

The foregoing and other objectives, features, and advantages of the invention will be more readily understood upon consideration of the following detailed description of the invention, taken in conjunction with the accompanying drawings.

BRIEF DESCRIPTION OF THE DRAWINGS

FIG. 1 is a side elevational view of a person's foot in a partially cut-away sock and shoe, showing a pair of protective devices according to the present invention in use.

FIG. 2 is a view of a person's hand and a portion of an arm covered by a cast.

FIG. 3 is a sectional view taken along line 3—3 of FIG. 2, showing a device according to the present invention in use to protect the skin of the person's arm.

FIG. 4 is a perspective view of one of the skin-protective devices shown in FIG. 1.

FIG. 5 is a section view, taken along line 5—5, of the skin-protective device shown in FIG. 4, showing the device attached to a person's skin.

FIG. 6 is a view similar to that of FIG. 5 showing a skin-protective device which is an alternative embodiment of the present invention.

FIG. 7 is a perspective view of a skin-protective device which is another alternative embodiment of the present invention.

FIG. 8 is a partially cut-away perspective view of a skin-protective device which is yet a further alternative embodiment of the present invention.

FIG. 9 is a perspective view of a skin-protective device embodying the present invention and including a padding member.

FIG. 10 is a perspective view of a skin-protective device embodying the present invention and including a padding member defining an opening to surround an area of a person's skin.

FIG. 11 is a perspective view of a device according to the present invention implanted in position to protect tendons from abrasion by an implanted plate.

FIG. 12 is a perspective view of a device according to the present invention located so as to protect a surgically repaired tendon.

DETAILED DESCRIPTION OF THE PREFERRED EMBODIMENTS

Referring now to the drawings which form a part of the disclosure herein, in FIG. 1 a person's foot 12 is inside a shoe 14, shown partly cut-away. A pair of devices according to the present invention, a larger skin-protective device 16 and a smaller skin-protective device 18, are both adhesively attached to the foot 12 to protect its skin against being irritated by movement of the foot 12 relative to the inner surface 13 of the shoe 14. A sock 15 is worn on the foot 12, between it and the inner surface 13 of the shoe 14, and the skin-protective devices of the present invention are shown being used between the foot 12 and the sock 15 within the shoe 14. Alternatively, the protective devices could be located between the sock 15 and the inner surface 13.

As shown in FIG. 1, the protective devices 16 and 18 are attached adhesively directly to the skin of the foot 12, but the same devices might also be adhered to or sewn or otherwise securely attached to the inside surface 13 of the shoe 14 or to either the inside or the outside of the sock 15. In each case, the skin-protective devices 16 and 18 serve to reduce the frictionally transmitted forces acting on the skin of the foot 12 as a result of movement of the inside surfaces 13 of the shoe 14 and sock 15 relative to the skin of the foot 12.

As shown in FIGS. 2 and 3, a skin-protective device 20 similar to the device 16 is attached adhesively to the skin of a person's arm 22 where the arm 22 is covered by a cast 24, to protect the skin from irritation as a result of relative movement between the skin and the inside of the cast 24. This can be of particular value in locations such as where bones, as at the wrist, are covered by only a thin layer of tissue including the skin. A similar situation could be found in the case of other orthopedic devices, such as in the attachment of a prosthetic limb, or where orthopedic braces bear against the skin of a natural limb.

The skin-protective devices 16, 18, and 20 are all of similar construction, except that their sizes are different, chosen to be applicable to each particular situation, so that the skin-protective device 16 utilized on the heel of the foot 12 is larger than the skin-protective device 18 used to protect the skin of a toe of the foot 12. As shown in FIG. 4, the protective device 16 comprises a pair of overlying parallel layers 26, 28 of a thin flexible membranous material attached to each other along respective peripheral margins, in a narrow area of connection indicated in broken line at 29, but otherwise not connected to each other. The layers 26 and 28 thus may be opposite sides of a flattened tube 30 of flexible, thin, synthetic plastic film. For example, the tube 30 may be of polyethylene, with a wall thickness of about 0.001 inch. The thickness used should be great enough to have strength to avoid being torn in use, but otherwise as thin as practical, to be able to conform easily and not to add to pressure on the skin by the thickness of the device 16. Alternatively, the layers 26 and 28 may be of a slippery yet porous material such as an expanded PTFE in order to allow moisture to evaporate from the skin through the device 16, enhancing comfort and enabling the skin to resist pressure and friction by helping to keep the skin dry.

Attached to a central area of the outer surface of the layer 26, that is, on the side of layer 26 facing away from the layer 28 and thus on the outside of the tube 30, is a layer 32 of an adhesive material. The adhesive material is preferably a flexible, pressuresensitive adhesive, covered until the device is to be used by a protective sheet 34 of a material such as a plastic-coated paper that can easily be peeled away from the layer 32 of adhesive material. The adhesive material of the layer 32 can be used to attach the protective device 16 to a person's skin or to an article of clothing such as the inside surface 13 of a shoe, or to a sock 15, at a location where the shoe or clothing is likely to be in contact with and to move relative to the adjacent skin. One suitable adhesive material is a hypoallergenic pressure sensitive acrylate adhesive, such as one available from 3M Medical Specialties Department, of St. Paul, Minn., in the form of product No. 1512, a transparent polyethylene film coated on both sides with the adhesive, and provided with a paper liner to serve as the protective sheet 34 in use.

As may be seen in FIG. 5, when the protective device 16 is attached to a person's skin 36 by the adhesive material 32, portions 38 and 40 of the layer 26 extend beyond the side margins 42 of the layer 32 of adhesive, which is located in and defines a central area of the layer 26. Similarly, portions 39 and 41 extend beyond the top margin 43 and a bottom margin of the layer 32 of adhesive material, although such extension of the top and bottom margins is of somewhat lesser importance.

The opposite inner surfaces 44 of the overlying layers 26 and 28, that is, the inner surfaces of the flattened tube 30, have a very small coefficient of friction relative to each other, preferably as a result of the material of which the overlying layers 26 and 28 are made. Thus, when a surface such as the inside surface 13 of the shoe 14 moves relative to the foot 12, particularly in either of the directions shown by the arrows 48 in FIGS. 1 and 5, the inside surfaces 44 slide along each other. The protective device 16 thus transmits only a very small amount of force between the inside surface 13 and the skin 36 by friction, so long as the extent of movement is limited. As the inside surfaces 44 slide along each other, one of the extending parts 38 and 40 of the layer 26 rolls from its original position into the position formerly occupied by a portion of the layer 28, as indicated by the arrows 50 in FIG. 5. Similarly, a portion of the layer 28 moves into a new position as an additional extension of the original location of the layer 26. As the layer 28 moves toward the right as shown in FIG. 5 the portions 38 and 40 of the flattened tube 30, extending beyond the central area where the adhesive layer 32 is located and including the connection portions 29 interconnecting the layers 26 and 28, assume the positions indicated by reference numerals 52. When the layer 28 moves leftward relative to the layer 26, the portions 38 and 40 and the connections 29 of the flattened tube 30 move toward the positions indicated by the reference numeral 54. Further movement of the layer 28 relative to the layer 26 is limited by the adhesive attachment of the device 16 to the skin 36 (or to a sock or a surface such as the inside surface 13, depending on where the device 16 is placed).

While the device 16 is shown in FIGS. 4 and 5 as having a significant distance between the opposing inside surfaces 44, the distance is actually greatly exaggerated in the drawings, to illustrate more clearly the rolling movement of the portions 38 and 40 as the inner surfaces 44 of the layers 26 and 28 slide along each other. In actual use of the device 16 the opposing inside surfaces 44 normally are directly in contact with each other. The tube-like structure of the device 16 provides the layers 26 and 28 freedom to move relative to each other farthest in the direction indicated by the arrows 48.

As mentioned above, ample flexibility of the material of which the layers 26 and 28 are made is desired. Such flexibility of the parts 38 and 40 extending beyond the margins 42 of the central area including adhesive material 32 permits movement of the layers 26 and 28 relative to each other in other directions, as well as the directions of the arrows 48. Thus the device 16 reduces the amount of friction where there is relative movement in any direction between an area of skin 36 being protected by the device 16 and an adjacent surface, such as the inside surface 13 of the shoe 14. However, since the freedom of movement of the layers 26 and 28 relative to each other is greatest in the direction indicated by the arrows 48, it is preferred to apply the device 16 to the skin 36 oriented in the way in which the greatest amount of expected relative movement of an adjacent surface against the skin 36 is parallel with the arrow 48.

Referring now to FIG. 6, in a slightly different embodiment of the invention a protective device 60 is generally similar to the protective device 16, and like reference numerals are used for like parts. The device 60 differs, however, in that between the inside surfaces 44 of the layers 26 and 28 there is provided a layer of a soft slippery material such as a piece 62 of a thin satin cloth. Such a slippery material is attached to an inside surface 44 of the layer 26, in an area preferably coextensive with or smaller than the area of the layer 32 of adhesive material, where it enhances the ability of the layers 26 and 28 to move relative to each other between the surface of the skin 36 and an adjacent surface such as the inside surface 13 of the shoe 14.

While the protective devices 16 and 60 have been illustrated as having the form of a flattened tube 30, it will be understood that it is also possible to manufacture such devices in more than one way, including placement of separately fashioned layers 26 and 28 of suitable material into appropriate positions overlying one another, and thereafter interconnecting respective marginal portions of those layers, to form the linear connections 29 between the layers 26 and 28 (FIG. 4). These connections 29 are preferably as smooth and flexible as practical, and are free to move as indicated by the arrows 50 (FIGS. 5, 6) as the layers 26 and 28 move relative to each other.

Depending upon the location on a person's skin where a protective device according to the invention is intended to be used, it may also be desirable to interconnect the layers 26 and 28 with each other as in the skin-protective device 66 shown in FIG. 7. There, the layers 26 and 28 are also held together by a narrow connection along a margin 68, so that the layers 26 and 28 are interconnected with each other along three sides of the rectangular skin-protective device 66 shown in FIG. 7. The layers 26 and 28 remain unconnected along the remaining margin 70, and are free to slide easily relative to each other with some flexure occurring along the margin 68.

A protective device 76, shown in FIG. 8, is generally similar to the device 66 shown in FIG. 7, except that both the bottom margin 68 and a top margin 78 of the device are closed by a linear connection so that the peripheral connections of the layer 26 to the layer 28 completely circumscribe, but are spaced outwardly apart from the central area including the layer 32 of adhesive material, forming a closed envelope of the two overlying layers 26 and 28. The resulting envelope may contain a very small amount of a lubricant, such as a few droplets 80 of a suitable oil or a small amount of a lubricant powder. The quantity of such a lubricant is intentionally kept small, so that it serves merely as a lubricant to permit the layers 26 and 28 to move relative to each other between a person's skin 36 and an opposing surface, without causing the protective device 76 to have a significant thickness that could increase the pressure of an adjacent surface of a shoe or other article against the skin intended to be protected by the device 76.

A protective device 86, shown in FIG. 9, includes structure generally similar to the protective device 16 shown in FIG. 4. Additionally, there is a thin pad 88 adhered to the outer surface of the layer 26, and a layer 90 of adhesive material overlies the thin pad 88. The adhesive material of the layer 90 is preferably limited to marginal portions of the thin pad 88, leaving a center part 92 of the pad 88 free from adhesive material. This center part 92 is thus available to absorb exudate from a blister or an area of previously irritated skin over which the skin-protective device 86 may be applied. Additionally, the thin pad 88 may be impregnated with medication prior to placement of the protective device 86 on a person's skin. The medication is thus held in contact with the underlying skin to promote healing while the protective device 86 reduces friction and thus protects the skin from further irritation and injury that might otherwise be caused by the rubbing of an adjacent surface of an article of clothing or the like.

A skin-protective device 96 shown in FIG. 10 is generally similar to the protective device 86 shown in FIG. 9, but in place of the thin pad 88 of the device 86 there is a thin pad 98 that defines an opening 100, surrounded by a layer 102 of an adhesive material. The thin pad 98 can thus be adhesively attached to a person's skin, surrounding a raised or swollen injured area such as a blister, providing some additional spacing between the irritated surface of the skin and an adjacent surface. At the same time, the protective device 96 reduces friction and allows the adjacent surface to move easily relative to the skin when it is attached to the skin.

A device according to the present invention may also be used internally, within a patient's body, to protect tissues which move with respect to each other in situations where surgery has created an abnormal situation, as where living tissue moves relative to a surgically implanted non-living object. For example, as shown in FIG. 11, a friction-reducing protective device 110 is used between a pair of tendons 112 extending closely alongside a fractured bone 114 whose parts have been stabilized with respect to each other by an implanted metal plate 116 attached to the bone by screws 118. In such a situation movement of the tendons, which normally occurs in a longitudinal direction as indicated by the arrow 120, would result in friction between the tendons 112 and the plate and screws 116, 118, except for the presence of the protective device 110 as shown.

The protective device 110 may be generally the same in its construction as one of the skin protective devices 16, 18, or 20, made of safely biologically implantable materials, and arranged so that the overlying parallel layers 122, 124 are connected to each other at locations 126 corresponding to the locations 29 in the device 16 shown in FIG. 4. Thus, as the tendons 112 move longitudinally as indicated by the arrow 120 with respect to the plate 116 and screws 118, the upper layer 124 of the protected device 110 moves with respect to the lower layer 122 together with the tendons 112, protecting the tendons 112 from irritating abrasion and friction as they move with respect to the bone 114.

The protective device 110 may be held in place by a suitable adhesive material (not shown) approved for use within a person's body, in a location as appropriate to attach the lower layer 122 to the plate 116. In many cases no specific fixation would be required, as soft tissue surrounding the tendons 112 will retain the protective device 110 suitably in a functional position. The protective device 110 could be left in place indefinitely, or could be removed at a later date when the plate 116 and screws 118 are removed, once the bone 114 has fully healed.

It will be appreciated that other forms of the protective device according to the present invention, prepared suitably for internal use, might also be desirable, as where a device similar to the protective device 60, shown in FIG. 6, could be used in order to provide a quantity of medication to the area protected by such a device. That is, by enclosing medication, or a small pad impregnated with a medication in a location corresponding to that of the piece 62 of satin cloth within the protective device 60 shown in FIG. 6, medication could be released to the surrounding tissues over an extended length of time. In some cases it might be desirable to have such a thin pad impregnated with medication located on an outer surface of one of the layers 122 and 124, similar to the placement of the thin pad 88 shown in FIG. 9.

Referring also to FIG. 12, an implantable protective device 130 may be used to surround or partially surround a tendon 132 which has been repaired by attaching portions of the tendon to each other by sutures 134. The protective device 130, which could be constructed generally similar to one of the previously described protective devices, is shown wrapped around the exterior of the repaired tendon 132 to permit movement of the tendon 132 longitudinally, as indicated by the arrow 136, with inner and outer membrane layers of the device 130 interconnected with each other along the ends 138 that extend circumferentially about the repaired tendon and, by rolling along the length of the tendon 132, permit the inner and outer layers of the protective device 130 to move with respect to each other with their opposed surfaces sliding over each other in the directions indicated by the arrow 136 to protect the sutures 134 from friction. Margins 140, 142 of the device 130 should lie close to and parallel with each other, and may be interconnected with each other by suitable adhesive material or by a few sutures 144 interconnecting the margins of the outer membrane to each other, or to adjacent soft tissue, providing that ample loose material is provided to permit the inner and outer layers of the protective device 130 to move relative to each other in a direction parallel with the arrow 136.

The terms and expressions which have been employed in the foregoing specification are used therein as terms of description and not of limitation, and there is no intention, in the use of such terms and expressions, of excluding equivalents of the features shown and described or portions thereof, it being recognized that the scope of the invention is defined and limited only by the claims which follow.

What is claimed is:

1. An internally useful tissue-protective device, comprising:
    (a) a pair of overlying parallel protective layers of biologically implantable membranous material overlying one another, each of said layers extending outwardly beyond a central area thereof;
    (b) said layers being joined to each other in a connection located outwardly apart from said central area; and
    (c) each of said layers having an inner face and an outer face, said inner faces confronting each other and being free to slide along each other over at least a limited distance.

2. The tissue-protective device of claim 1, further including a layer of a biologically implantable adhesive material located wholly within said central area, on an outer face of one of said layers.

3. The tissue-protective device of claim 1, said connection including a narrow strip extending along a peripheral line spaced outwardly apart from said central area.

4. The tissue-protective device of claim 1, said layers of membranous material including respective portions of a collapsed tube having a thin flexible wall structure and a pair of open ends, each of said layers including a portion of a respective one of a pair of opposite sides of said tube.

5. The tissue-protective device of claim 1 wherein each of said layers of membranous material is a thin film of a synthetic plastic material.

6. The tissue-protective device of claim 1 wherein said connection completely circumscribes said central area, and wherein a quantity of a lubricant is enclosed between said layers within an area defined by said connection.

7. The tissue-protective device of claim 1 including an absorbent layer attached to one of said layers of membranous material, between said outer face thereof and said layer of adhesive material.

8. The tissue-protective device of claim 7 wherein said absorbent layer is medicated.

9. The tissue-protective device of claim 7 wherein said absorbent layer defines an opening therethrough.

10. The tissue-protective device of claim 1 including a removable adhesive-protecting sheet attached to and covering said layer of adhesive material.

11. The tissue-protective device of claim 1 wherein at least one of said layers of membranous material is of porous material.

12. The tissue-protective device of claim 1 wherein said layers of membranous material are separate and free to move relative to each other along at least a part of a periphery of said device.

13. The tissue-protective device of claim 1 wherein a portion of one of said layers is attached to an article of clothing.

14. The tissue-protective device of claim 1 wherein said connection completely circumscribes said central area, and wherein a quantity of a medication is enclosed between said layers within an area defined by said connection.

15. The tissue-protective device of claim 1 wherein a quantity of a medication is enclosed between said layers within an area defined by said connection.

16. A method of protecting living tissue against frictional irritation, comprising the steps of:
   (a) placing a device including a pair of layers of thin flexible biologically implantable membranous material between an area of tissue surface intended to be protected and an adjacent surface confronting said area of tissue surface;
   (b) attaching one of said layers to a selected one of said area of tissue surface and said adjacent surface by the use of an adhesive, said pair of layers thereby separating said area of tissue surface from said adjacent surface; and
   (c) in response to movement of said adjacent surface relative to said area of tissue surface, moving said layers of membranous material along one another over a limited range of movement, with a coefficient of friction between said layers that is substantially smaller than a coefficient of friction that would be present between said area of tissue surface and said adjacent surface absent said pair of layers.

17. The method of claim 16 including the further step of providing a layer of an absorbent material impregnated with a quantity of medication between said layers of membranous material and causing at least a portion of said medication to be delivered therefrom to tissue located adjacent said device.

18. The method of claim 17 wherein at least a part of said membranous material is porous, including the step of gradually delivering said medication through said porous membranous material.

19. The method of claim 16 wherein said adjacent surface is a surface of an implanted non-living object.

20. A tissue-protective device, comprising:
   (a) a pair of overlying parallel protective layers of membranous material overlying one another, each of said layers extending outwardly beyond a central area thereof;
   (b) said layers being joined to each other in a connection located outwardly apart from said central area;
   (c) each of said layers having an inner face and an outer face, said inner faces confronting each other and being free to slide along each other over at least a limited distance.

* * * * *